(12) United States Patent
Wahi

(10) Patent No.: US 8,163,802 B2
(45) Date of Patent: Apr. 24, 2012

(54) ELECTROSTATICALLY CHARGED MULTI-ACTING NASAL APPLICATION, PRODUCT, AND METHOD

(75) Inventor: Ashok Wahi, Hillsborough, NJ (US)

(73) Assignee: Trutek Corp., Hillsborough, NJ (US)

( * ) Notice: Subject to any disclaimer, the term of this patent is extended or adjusted under 35 U.S.C. 154(b) by 316 days.

(21) Appl. No.: 12/467,271

(22) Filed: May 16, 2009

(65) Prior Publication Data

US 2010/0004337 A1 Jan. 7, 2010

Related U.S. Application Data

(60) Provisional application No. 61/085,855, filed on Aug. 3, 2008, provisional application No. 61/078,478, filed on Jul. 7, 2008.

(51) Int. Cl.
*A61K 31/198* (2006.01)
*A61K 31/14* (2006.01)

(52) U.S. Cl. ........................................ 514/564; 514/643

(58) Field of Classification Search .................. 514/564, 514/643; 128/206.11
See application file for complete search history.

(56) References Cited

U.S. PATENT DOCUMENTS

| | | | |
|---|---|---|---|
| 1,071,015 A | 8/1913 | Adler |
| 2,237,954 A | 4/1941 | Wilson |
| 2,433,565 A | 12/1947 | Korman |
| 2,751,906 A | 10/1953 | Irvine |
| 2,777,442 A | 1/1957 | Zelano |
| 3,145,711 A | 8/1964 | Beber |
| 3,513,839 A | 5/1970 | Vacante |
| 4,030,491 A | 6/1977 | Mattila |
| 4,052,983 A | 10/1977 | Bovender |
| 4,267,831 A | 5/1981 | Aguilar |
| 4,401,117 A | 8/1983 | Gershuny |
| 4,789,504 A | 12/1988 | Ohmori et al. |
| 4,874,659 A | 10/1989 | Ando et al. |
| 5,468,488 A | 11/1995 | Wahi |
| 5,674,481 A | 10/1997 | Wahi |
| 6,844,005 B2 | 1/2005 | Wahi |
| 2003/0223934 A1 | 12/2003 | Wahi |

*Primary Examiner* — Raymond Henley, III
(74) *Attorney, Agent, or Firm* — Stanley H. Kremen

(57) ABSTRACT

A product to reduce and method of reducing the risk of inhalation of harmful substances by applying a formulation composition to a substrate or the skin in close proximity of one or more nostrils. This formulation, when applied creates an electrostatic field having a charge. The electrostatic field attracts airborne particulates of opposite charge to the substrate that are in close proximity to the substrate close to the skin and a biocidic agent renders microorganisms coming in contact the substrate or skin less harmful.

23 Claims, No Drawings

ELECTROSTATICALLY CHARGED MULTI-ACTING NASAL APPLICATION, PRODUCT, AND METHOD

CROSS REFERENCE TO RELATED APPLICATIONS a) The Present application is the non-provisional counterpart of my pending U.S. Provisional Patent Application Ser. No. 61/085,555 (the '555 application) filed on Aug. 3, 2008 which is incorporated by reference in its entirety herein. The Present application claims the benefit of and priority to said '555 application.

b) The Present application is also the non-provisional counterpart of my pending U.S. Provisional Patent Application Ser. No. 61/078,478 (the '478 application) filed on Jul. 7, 2008 which is incorporated by reference in its entirety herein. The Present application claims the benefit of and priority to said '478 application.

c) The Present application is likewise related to my prior U.S. Provisional Patent Application Ser. No. 60/570,103 (the '103 application) filed on May 12, 2004 (now expired), and which is incorporated by reference in its entirety herein. The '478 application provides a virtually identical disclosure to the '103 application.

d) Furthermore, the Present application is related to my pending U.S. Provisional Application Ser. No. 61/078,472 filed on Jul. 7, 2008, which is incorporated by reference in its entirety herein.

e) The Present application is also related to my prior U.S. Provisional Patent Application Ser. No. 60/598,462 filed on Aug. 3, 2004 (now expired), and which is incorporated by reference in its entirety herein.

f) The Present application is additionally related to my U.S. Pat. No. 5,468,488, entitled "ELECTROSTATICALLY CHARGED NASAL APPLICATION PRODUCT AND METHOD" issued on Nov. 21, 1995. This patent is incorporated by reference in its entirety herein.

g) The Present application is further related to my U.S. Pat. No. 5,674,481, entitled "ELECTROSTATICALLY CHARGED NASAL TOPICAL APPLICATION PRODUCT" issued on Oct. 7, 1997. This patent is incorporated by reference in its entirety herein.

h) The Present application is moreover related to my U.S. Pat. No. 6,844,005 entitled "ELECTROSTATICALLY CHARGED NASAL APPLICATION PRODUCT WITH INCREASED STRENGTH" issued on Jan. 18, 2005. This patent is incorporated by reference in its entirety herein.

i) Finally, this application is furthermore related to US Non-Provisional Utility patent application Ser. No. 10/082,978 entitled "ELECTROSTATICALLY CHARGED NASAL APPLICATION PRODUCT WITH INCREASED STRENGTH" filed on Feb. 25, 2002. This patent application is incorporated by reference in its entirety herein.

FIELD OF THE INVENTION

The Present Invention relates to the field of protective compositions against assault by various irritants and noxious substances as well as against assault by assorted microorganisms that typically gain entry into the body through the airway and/or nasal mucosa. The Present Invention also relates to anti-viral, anti-bacterial, and anti-microbial products and methods that involve the use of products heretofore developed for restricting the flow of airborne contaminants into the nasal passages by creating an electrostatic field in an area near about the nasal passages. This reduced the inflow of airborne contaminants to the nasal passages by capturing the contaminants and keeping them from entering the body. In the present invention, these electrostatically charged nasal application products capture and hold the contaminants including viruses, bacteria, and other harmful microorganisms or toxic particulates, inactivate them dermally outside the body and render them harmless.

BACKGROUND OF THE INVENTION

The nasal passages and nasal mucosa serve as body entry points for a wide variety of noxious and toxic substances. The body's immune system responds with certain relatively harmless irritants to the nasal passages and airways with reflex responses such as coughing and sneezing. This merely reintroduces the irritants into the environment. However, when the irritant comprises microorganisms, especially those that reproduce within the body and that are transmitted by coughing and sneezing, others may become infected. When a person feels a cough or a sneeze coming on, he merely covers his nose and mouth. However, if that person is contagious, this action does little to prevent others from also becoming infected. Furthermore, the use of a tissue or handkerchief for this purpose is extremely inefficient. This limits the protection of an individual from becoming infected or infecting others.

Other means of dealing with preventing inhalation of harmful or irritating substances or of infections agents include wearing facemasks to filter out these irritants. An example of this is the simple dust mask, typically found in the hardware store or medical supply store. However, even these are inadequate and inefficient. In many localities, during flu season, one can see a large number of people wearing these dust masks in public places. The dust masks are now known to be ineffective. Another example of this preventative method is the gas mask, which is more efficient than the dust mask. Yet, even gas masks are not highly efficient with respect to microscopic and sub-microscopic microorganisms. Furthermore, they are extremely cumbersome and cannot generally be used during normal day-to-day activities.

Patents such as U.S. Pat. No. 6,844,005 describe electrostatically charged compositions that may be applied externally in the vicinity of the nostril and attract oppositely charged materials that would otherwise be inhaled. However, those compositions simply create an electrostatic field that helps to filter out oppositely charged materials. While this action may offer suitable protection against particles that are inhaled passively, they suffer from the fact that they cannot completely deal with particulates that have their own internal means of overcoming the electrostatic forces, such as microorganisms that are motile within the air stream. Furthermore, actions by the person having those electrostatic compositions in the vicinity of the nostrils can sufficiently displace the offending particles or organisms, especially in such instances as blowing or wiping the nose, so that particles that were held captive by the former compositions could become dislodged, again set free, and be inhaled.

OBJECTS OF THE INVENTION

It is therefore an object of the invention to provide a composition that can be readily applied to the exterior region around the nostril and/or slightly inside the edge of the nostril or near the vicinity of the source of release with method and compositions capable of capturing particulates and microorganisms.

It is another object of the invention to have the capability to hold it for a duration from being dislodged in to the air stream again.

It is a further object of the invention to provide a composition that can be applied near the vicinity of the source of release or to the area around the exterior of and/or slightly inside the edge of the nostril that will inactivate, kill, or render harmless a microorganism, which has been captured and held by the composition.

It is yet another object of the invention to provide a composition that can be applied to a filter substrate for improving the substrates ability to trap and hold particulates and microorganisms and to simultaneously inactivate, kill, or render harmless the microorganisms so trapped. Such filter substrate could be placed in the close proximity of the skin near the path of inhalation, near the source of release of such particulates while the inhaler is at a distance or both.

It is still another object of the invention to provide a method of prophylactically preventing or of substantially reducing the risk of infection by an infectious agent without the utilization of ingested antiviral and/or antibacterial agents.

Yet other objects of the invention will be apparent to those of ordinary skill once having benefit of the instant disclosure. In all of the foregoing objects, the deficiencies of the previously mentioned prior art are overcome by the teachings of this invention.

SUMMARY OF THE INVENTION

These and other objects of the invention are unexpectedly achieved by an electrostatically charged composition having at least one polymeric quaternary compound in an aqueous or non-aqueous based formulation, which when applied to a surface, creates an electrostatic field such that oppositely charged airborne particulates (including microorganisms) in the vicinity of the surface are electrostatically trapped, held thereto and one or more of the microorganisms so captured is neutralized, killed, inactivated, and rendered harmless.

DETAILED DESCRIPTION OF THE INVENTION

The present invention relates to anti-microorganism, anti-viral/anti-bacterial products and methods that involve the use of products that restrict the flow of airborne contaminants into the nasal passages by creating an electrostatic field in an area near about the nasal passages. Additionally, in the present invention, these electrostatically charged nasal application products are used to hold the contaminants including microorganisms, viruses, bacteria, and other harmful or toxic particulate outside the body and render them harmless.

Emergencies of Anthrax lead to the concept of avoidance of inhaling airborne microscopic and sub-microscopic contaminants. It is the intention of the Present Invention to filter and render harmless materials such as anthrax spores, human corona virus, smallpox virus, influenza virus, avian flu virus, swine flu virus, rhino virus, and other biological or chemical elements/toxins/irritants, and the like, prior to their entering the nasal passages.

Airborne microorganisms are a major cause of respiratory ailments in humans, causing allergies, asthma, and pathogenic infections of the respiratory tract. Airborne fungal spores are also important agents that spread diseases. Respiratory diseases cause many fatalities and are a cause of great concern. During a sneeze, millions of tiny droplets of water and mucus are expelled at a high velocity. The droplets contain viral particles and/or bacteria. This is a means of transmission of several diseases by inhaled airborne particles as follows:

| VIRAL DISEASES (virus type in brackets) | BACTERIAL DISEASES (bacterial name in brackets) |
|---|---|
| Chickenpox (Varicella) | Whooping cough (*Bordetella pertussis*) |
| Flu (Influenza) | Meningitis (*Neisseria* species) |
| Measles (Rubeola) | Diphtheria (*Corynebacterium diphtheriae*) |
| German measles (Rubella) | |
| Mumps (Mumps) | Pneumonia (*Mycoplasma pneumoniae, Streptococcus* species) |
| Smallpox (Variola) | |
| SARS (Human Corona) | Tuberculosis (*Mycobacterium tuberculosis*) |
| | Anthrax (*Anthracsis* bacterium) |

Diseases caused by environmental particulates include, but are not limited to the following:

| ENVIRONMENTAL PARTICULATE DISEASES | SOURCE |
|---|---|
| Psittacosis (*Chlamydia psittaci*) | Dried, powdery droppings from infected birds (parrots, pigeons, etc.) |
| Legionnaire's disease (*Legionella pneumophila*) | Droplets from air-conditioning systems, water storage tanks, etc., where the bacterium grows. |
| Acute allergic alveolitis (various fungal and actinomycete spores) | Fungal or actinomycete spores from decomposing organic matter (composts, grain stores, hay, etc.) |
| Aspergillosis (*Aspergillus fumigatus, A. flavus, A. niger*) | Fungal spores inhaled from decomposing organic matter. |
| Histoplasmosis (*Histoplasma capsulatum*) | Spores of the fungus, in old, weathered bat or bird droppings. |
| Coccidioidomycosis (*Coccidioides immitis*) | Spores in air-blown dust in desert regions (Central, South and North America) where the fungus grows in the soil. |

To accomplish the present invention, a formulation having at least one polyquaternary ammonium compound is prepared, such compounds, alone or together capable of creating an electrostatic field on and around a surface to which it is applied, including surfaces such as skin, textile (woven and non-woven), and hard surfaces, such as floors, walls, wood, metal, plastic, etc. The formulation is generally aqueous based, but may include non-aqueous solvents used which are compatible with the other formulation components and the application surface to which it is applied. Preferably, the formulation is an aqueous formulation. In addition to the polyquaternary ammonium compound, the composition includes at least. Furthermore, the composition may contain, but is not required to contain various thickeners, gellants, fragrances, colorants, emollients, humectants, and generally other suitable components that are compatible with the end use application and the other components of the formulations. Thus, a composition of the invention that is intended to be applied to a filter substrate that is perhaps used as a mask with an additional liner between a user and the filter substrate may utilize materials that would not be compatible with direct contact with skin, although it is preferable that all of the components are compatible with direct application to the skin as a means of limiting reaction due to inadvertent contact between the composition and the skin.

A formulation of the invention comprises:
water,
at least one quaternary thickener, a preservative,
a conditioner,
an emulsifier,
a biocidic agent, and
a neutralizing agent added to adjust and achieve a pH in the range of 5.0 to 6.8.

It may further comprise without limitation a combination of the following:
a surfactant,
a thickener,
an emollient,
a humectant, and
a binder.

In an exemplary embodiment of such a formulation, a quaternary thickener may comprise without limitation, at least one of the following:
Polyquaternium-10
Polyquaternium-22
Polyquaternium-67
Polyquaternium-70
Polyquaternium-72
Polyquaternium-88
Cocodimonium Hydroxypropyl Hydrolyzed Keratin
Hydroxypropyltrimonium Wheat Protein Benzalkonium Chloride may also serve the same function, but it is also a cationic agent as well as a biocide. Another biocide that may be used is Lysine HCL.

In an exemplary embodiment of such a formulation, an emulsifier may comprise without limitation, at least one of the following:
Cetyl Alcohol (which can also serve as a thickener)
Cetearyl Alcohol
Glyceryl Stearate
Ceteareth-20
PEG-40 Stearate
Dicetyl Phosphate
Ceteth-10 Phosphate In an exemplary embodiment of such a formulation, the emollient may be Isocetyl Behenate without limitation. The thickener may be Cetyl Alcohol or Stearyl Alcohol without limitation.

In an exemplary embodiment of such a formulation, a preservative may comprise without limitation, at least one of the following:
Phenoxyethanol;
Methylparaben;
Butylparaben;
Ethylparaben;
Propylparaben;
Isobutylparaben.

Examples of typical formulations found to be effective appear in the ten tables that follow. Percentages are given by weight.

TABLE 1

| Ingredient | Percent Range | Function |
| --- | --- | --- |
| Water | 62%-80% | Solvent, Moisturizer |
| Gluconolactone, Sodium Benzoate | 1% | Preservative |
| Lysine HCL | 1% | Conditioner |
| Polyquaternium - 67 | 3%-6% | Conditioner |
| Octoxynol - 9 | 2%-5% | Surfactant |
| Polyquaternium - 72 | 6%-10% | Conditioner |
| Polyquaternium - 70 | 0.5%-1% | Conditioner |
| Dipropylene Glycol | | |
| Isocetyl Behenate | 4%-6% | Emollient |
| Stearyl Alcohol | 1%-3% | Thickener |
| Cetyl Alcohol | 0.25%-1% | Thickener |
| Ceteareth - 20, PEG - 40 Stearate, Cetearyl Alcohol | 1%-2% | Emulsifier |
| Water, Hydrolyzed Algin | 0.5%-1.5% | Conditioner |
| Hydrolized Soy Protein | 0.25%-1% | Conditioner |

TABLE 2

| Ingredient | Percent Range | Function |
| --- | --- | --- |
| Water | 72%-88% | Solvent, Moisturizer |
| Phenoxyethanol, Methylparaben, Propylparaben, Butylparaben, Ethylparaben, Isobutylparaben | 1% | Preservative |
| Lysine HCL | 1% | Conditioner, Biocide |
| Polyquaternium - 67 | 3%-6% | Conditioner, Quaternary |
| Nonoxynol - 10 | 2%-4% | Surfactant |
| Cocodimonium Hydroxypropyl Hydrolyzed Keratin | 0.5%-2% | Conditioner, Quaternary |
| Polyquaternium - 72 | 0.5%-2% | Conditioner, Quaternary |
| Polyquaternium - 88 | 1%-4% | Conditioner, Quaternary |
| Cetearyl Alcohol, Glyceryl Stearate Emulsifier, PEG - 40 Stearate, Ceteareth - 20 | 1%-4% | Emulsifier |
| Cetearyl Alcohol, Dicetyl Phosphate, Ceteth - 10 Phosphate | 0.5% | Emulsifier |
| Benzalkonium Chloride | 0.25%-1% | Cationic, Quaternary, Biocide |
| Hydroxypropyltrimonium Wheat Protein | 1% | Conditioner, Quaternary |
| Sodium Hydroxide | 0.01%-0.05% | Neutralizing Agent |

TABLE 3

| Ingredient | Percent Range | Function |
| --- | --- | --- |
| Water | 67%-87% | Solvent, Moisturizer |
| Phenoxyethanol, Methylparaben, Propylparaben, Butylparaben, Ethylparaben, Isobutylparaben | 1% | Preservative |
| Lysine HCL | 1% | Conditioner, Biocide |
| Polyquaternium - 67 | 3%-7% | Conditioner, Quaternary |
| Polyquaternium - 72 | 3%-7% | Conditioner, Quaternary |
| Cocodimonium Hydroxypropyl Hydrolized Keratin | 1%-4% | Conditioner, Quaternary |
| Polyquaternium - 88 | 1%-4% | Conditioner, Quaternary |
| Cetyl Alcohol | 1.5%-2.5% | Thickener |
| Cetearyl Alcohol, Glyceryl PEG - 40 Stearate, Ceteareth - 20 | 1%-4% | Emulsifier |
| Benzalkonium Chloride | 0.25%-1% | Cationic, Quaternary, Biocide |
| Hydroxypropyltrimonium Wheat Protein | 1% | Conditioner, Quaternary |
| Sodium Hydroxide | .025%-.075% | Neutralizing Agent |

TABLE 4

| Ingredient | Percent Range | Function |
| --- | --- | --- |
| Water | 71%-83% | Solvent, Moisturizer |
| Phenoxyethanol, Methylparaben, Propylparaben, Butylparaben, Ethylparaben, Isobutylparaben | 1% | Preservative |
| Lysine HCL | 1% | Conditioner, Biocide |
| Polyquaternium - 67 | 4%-6% | Conditioner, Quaternary |
| Polyquaternium - 72 | 4%-6% | Conditioner, Quaternary |
| Cocodimonium Hydroxypropyl Hydrolyzed Keratin | 2%-4% | Conditioner, Quaternary |
| Polyquaternum - 88 | 1%-3% | Conditioner, Quaternary |
| Cetyl Alcohol | 2% | Thickener |
| Cetearyl Alcohol, Glyceryl Stearate, PEG - 40 Stearate, Ceteareth - 20 | 1%-3.5% | Emulsifier |
| Benzalkonium Chloride | 0.25%-1% | Cationic, Quaternary, Biocide |
| Hydroxypropyltrimonium Wheat Protein | 1% | Conditioner, Quaternary |
| Sodium Hydroxide | .025%-.075% | Neutralizing Agent |

TABLE 5

| Ingredient | Percent Range | Function |
| --- | --- | --- |
| Water | 73%-85% | Solvent, Moisturizer |
| Phenoxyethanol, Methylparaben, Propylparaben, Butylparaben, Ethylparaben, Isobutylparaben | 1% | Preservative |
| Lysine HCL | 1% | Conditioner, Biocide |
| Polyquaternium - 67 | 2%-3% | Conditioner, Quaternary |
| Polyquaternium - 72 | 4%-6% | Conditioner, Quaternary |
| Cocodimonium Hydroxypropyl Hydrolyzed Keratin | 2%-4% | Conditioner, Quaternary |
| Polyquaternium - 88 | 1%-3% | Conditioner, Quaternary |
| Cetyl Alcohol | 2% | Thickener |
| Cetearyl Alcohol, Glyceryl Stearate, PEG - 40 Stearate, Ceteareth - 20 | 1%-3% | Emulsifier |
| Benzalkonium Chloride | 0.25%-1% | Cationic, Quaternary, Biocide |
| Hydroxypropyltrimonium Wheat Protein | 1% | Conditioner, Quaternary |
| Sodium Hydroxide | 0.05%-0.75% | Neutralizing Agent |

TABLE 6

| Ingredient | Percent Range | Function |
| --- | --- | --- |
| Water | 69%-85% | Solvent, Moisturizer |
| Phenoxyethanol, Methylparaben, Propylparaben, Butylparaben, Ethylparaben, Isobutylparaben, | 1% | Preservative |
| Lysine HCL | 1% | Conditioner, Biocide |
| Polyquaternium - 10 | 0.25%-0.85% | Conditioner, Quaternary |
| Polyquaternium - 67 | 1.5%-3.5% | Conditioner, Quaternary |
| Polyquaternium - 72 | 4%-6% | Conditioner, Quaternary |
| Cetyl Alcohol | 1%-3% | Thickener |
| Cocodimonium Hydroxypropyl Hydrolyzed Keratin | 2%-4% | Conditioner, Quaternary |
| Polyquaternium - 88 | 1%-3% | Conditioner, Quaternary |
| Polyquaternium - 22 | 1%-3% | Conditioner, Quaternary |
| Cetearyl Alcohol, Glyceryl Stearate, PEG - 40 Stearate, Ceteareth - 20 | 1%-3% | Emulsifier |
| Benzalkonium Chloride | 0.25%-1% | Conditioner, Quaternary, Biocide |
| Hydroxypropyltrimonium Wheat Protein | 1% | Conditioner, Quaternary |
| Sodium Hydroxide | 0.05%-0.75% | Neutralizing Agent |

TABLE 7

| Ingredient | Percent Range | Function |
| --- | --- | --- |
| Water | 67%-86% | Solvent, Moisturizer |
| Phenoxyethanol, Methylparaben, Butylparaben, Ethylparaben, Isobutylparaben | 1% | Preservative |
| Lysine HCL | 1% | Conditioner, Biocide |
| Polyquaternium - 10 | 1%-4% | Conditioner, Quaternary |
| Polyquaternium - 67 | 1%-4% | Conditioner, Quaternary |
| Polyquaternium - 72 | 0.5%-1.5% | Conditioner, Quaternary |
| Cocodimonium Hydroxypropyl Hydrolized Keratin | 0.5%-1.5% | Conditioner, Quaternary |
| Microcare Quat CTC 30 | 1%-3% | Conditioner, Quaternary |
| Polyquaternium - 88 | 1%-3% | Conditioner, Quaternary |
| Polyquaternium - 22 | 1%-3% | Conditioner, Quaternary |
| Cetyl Alcohol | 3%-5% | Thickener |
| Cetearyl Alcohol, Glyceryl Stearate, PEG - 40 Stearate, Ceteareth - 20 | 2%-3% | Emulsifier |
| Benzalkonium Chloride | 0.25%-1% | Conditioner, Quaternary, Biocide |
| Hydroxypropyltrimonium Wheat Protein | 1% | Conditioner, Quaternary |
| Sodium Hydroxide | 0.05%-0.1% | Neutralizing Agent |

TABLE 8

| Ingredient | Percent Range | Function |
| --- | --- | --- |
| Water | 58%-74% | Solvent, Moisturizer |
| Phenoxyethanol, Methylparaben, Propylparaben, Butylparaben, Ethylparaben, Isobutylparaben | 1% | Preservative |
| Lysine HCL | 1% | Conditioner, Biocide |
| Glycerin | 10% | Humectant |
| Glyceryl Acetate/Acrylic Acid Copolymer | 1% | Conditioner, Humectant |
| Polyquaternium - 10 | 1%-4% | Conditioner, Quaternary |
| Polyquaternium - 67 | 1%-3% | Conditioner, Quaternary |
| Polyquaternium - 72 | 0.5%-1.5% | Conditioner, Quaternary |
| Cocodimonium Hydroxypropyl Hydrolyzed Keratin | 0.5%-1.5% | Conditioner, Quaternary |
| Cetrimonium Chloride | 1%-3% | Conditioner, Quaternary |
| Polyquaternium - 88 | 1%-3% | Conditioner, Quaternary |
| Polyquaternium - 22 | 1%-3% | Conditioner, Quaternary |
| Cetyl Alcohol | 4% | Thickener |
| Cetearyl Alcohol, Glyceryl Stearate, PEG - 40 Stearate, Ceteareth - 20 | 2%-3% | Emulsifier |
| Polybutene | 4% | Binder |
| Benzalkonium Chloride | 0.25%-1% | Conditioner, Quaternary, Biocide |

TABLE 8-continued

| Ingredient | Percent Range | Function |
|---|---|---|
| Hydroxypropyltrimonium Wheat Protein | 1% | Conditioner, Quaternary |
| Sodium Hydroxide | .0.05%-0.1% | Neutralizing Agent |

TABLE 9

| Ingredient | Percent Range | Function |
|---|---|---|
| Water | 54%-73% | Solvent, Moisturizer |
| Phenoxyethanol, Methylparaben, Propylparaben, Butylparaben, Ethylparaben, Isobutylparaben | 1% | Preservative |
| Lysine HCL | 1% | Conditioner, Biocide |
| Glycerin | 8% | Humectant |
| Glyceryl Acetate/Acrylic Acid Copolymer | 1% | Conditioner, Humectant |
| Polyquaternium - 10 | 1%-4% | Conditioner, Quaternary |
| Polyquaternium - 67 | 1%-4% | Conditioner, Quaternary |
| Polyquaternium - 72 | 0.5%-2% | Conditioner, Quaternary |
| Cocodimonium Hydroxypropyl Hydrolyzed Keratin | 0.5%-2% | Conditioner, Quaternary |
| Cetrimonium Chloride | 1%-3% | Conditioner, Quaternary |
| Polyquaternium - 88 | 1%-3% | Conditioner, Quaternary |
| Polyquaternium - 22 | 1%-3% | Conditioner, Quaternary |
| Cetyl Alcohol | 4% | Thickener |
| Cetearyl Alcohol, Glyceryl Stearate, PEG - 40 Stearate, Ceteareth - 20 | 2%-3% | Emulsifier |
| Polybutene | 3%-4% | Binder |
| Benzalkonium Chloride | 0.25%-1% | Conditioner, Quaternary, Biocide |
| Hydroxypropyltrimonium Wheat Protein | 1% | Conditioner, Quaternary |
| Sodium Hydroxide | 0.05%-0.1% | Neutralizing Agent |

TABLE 10

| Ingredient | Percent Range | Function |
|---|---|---|
| Water | 52%-71% | Solvent, Moisturizer |
| Phenoxyethanol, Methylparaben, Propylparaben, Butylparaben, Ethylparaben, Isobutylparaben | 1% | Preservative |
| Lysine HCL | 1% | Conditioner, Biocide |
| Glycerin | 9% | Humectant |
| Glyceryl Acetate/Acrylic Acid Copolymer | 1% | Conditioner, Humectant |
| Polyquaternium - 10 | 1%-3.5% | Conditioner, Quaternary |
| Polyquaternium - 67 | 1%-3% | Conditioner, Quaternary |
| Polyquaternium - 72 | 0.5%-2% | Conditioner, Quaternary |
| Cocodimonium Hydroxypropyl Hydrolyzed Keratin | 0.5%-2% | Conditioner, Quaternary |
| Cetrimonium Chloride | 1%-3% | Conditioner, Quaternary |
| Polyquaternium - 88 | 1%-3% | Conditioner, Quaternary |
| Polyquaternium - 22 | 1%-3% | Conditioner, Quaternary |
| Cetyl Alcohol | 4% | Thickener |
| Cetearyl Alcohol, Glyceryl Stearate, PEG - 40 Stearate, Ceteareth - 20 | 1%-4% | Emulsifier |
| Polybutene | 5%-6% | Binder |
| Benzalkonium Chloride | 0.25%-1% | Conditioner, Quaternary, Biocide |
| Hydroxypropyltrimonium Wheat Protein | 1% | Conditioner, Quaternary |
| Sodium Hydroxide | 0.05%-0.1% | Neutralizing Agent |

All of the formulations described in TABLE 1-10 representing various embodiments of the Present Invention operate in the manner that was disclosed herein. The same results may be achieved by varying the percentages for the active and inactive ingredients. Varying the percentages for the active ingredients affects the potency of the formulation. Varying the percentages for the inactive ingredients affects the consistency of the formulation. The desired results may be achieved by varying the ingredients and their amounts by those skilled in the art without undue experimentation.

I claim:

1. A method for electrostatically inhibiting harmful particulate matter from infecting an individual through nasal inhalation wherein a formulation is applied to skin or tissue of nasal passages of the individual in a thin film, said method comprising:
   a) electrostatically attracting the particulate matter to the thin film;
   b) holding the particulate matter in place by adjusting the adhesion of the thin film to permit said thin film to stick to the skin or tissue and by adjusting the cohesion of the formulation to provide adequate impermeability to the thin film; and,
   c) inactivating the particulate matter by adding at least one ingredient that would render said particulate matter harmless.

2. A formulation for electrostatically inhibiting harmful particulate matter from infecting an individual through nasal inhalation wherein the formulation is applied to skin or tissue of nasal passages of the individual in a thin film, said formulation comprising at least one cationic agent and at least one biocidic agent, and wherein said formulation, once applied:
   a) electrostatically attracts the particulate matter to the thin film;
   b) holds the particulate matter in place by adjusting the adhesion of the thin film to permit said thin film to stick to the skin or tissue and by adjusting the cohesion of the formulation to provide adequate impermeability to the thin film; and,
   c) inactivates the particulate matter and renders said particulate matter harmless.

3. The formulation of claim 2 wherein the at least one cationic agent is a polymeric quaternary ammonium compound.

4. The formulation of claim 3 wherein the at least one polymeric quaternary ammonium compound is taken from the group consisting of:
   Polyquaternium-10,
   Polyquaternium-22,
   Polyquaternium-67,
   Polyquaternium-70,
   Polyquaternium-72, and
   Polyquaternium-88.

5. The formulation of claim 2 wherein the at least one cationic agent is Cocodimonium Hydroxypropyl Hydrolyzed Keratin or Hydroxypropyltrimonium Wheat Protein.

6. The formulation of claim 2 wherein the at least one cationic agent is Benzalkonium Chloride.

7. The formulation of claim 2 wherein the at least one biocidic agent is Benzalkonium Chloride or Lysine HCL.

8. A formulation for electrostatically inhibiting harmful particulate matter from infecting an individual through nasal inhalation wherein the formulation is applied to skin or tissue of nasal passages of the individual in a thin film, said formulation comprising:

a) at least one biocidic agent, and b) at least one quaternary thickener.

9. The formulation of claim 8 wherein the at least one biocidic agent is Benzalkonium Chloride or Lysine HCL.

10. The formulation of claim 8 wherein the at least one quaternary thickener is taken from the group consisting of:

Polyquaternium-10,

Polyquaternium-22,

Polyquaternium-67,

Polyquaternium-70,

Polyquaternium-72, and

Polyquaternium-88.

11. The formulation of claim 8 wherein the at least one cationic agent is Cocodimonium Hydroxypropyl Hydrolyzed Keratin or Hydroxypropyltrimonium Wheat Protein.

12. The formulation of claim 8 wherein the at least one cationic agent is Benzalkonium Chloride.

13. The formulation of claim 8 further comprising:

a) water, b) a preservative, c) a conditioner, and d) an emulsifier.

14. The formulation of claim 13 further comprising a neutralizing agent added to adjust a pH in the range of 5.0 to 6.8.

15. The formulation of claim 13 further comprising a surfactant.

16. The formulation of claim 13 further comprising a thickener.

17. The formulation of claim 13 further comprising an emollient.

18. The formulation of claim 13 further comprising a humectant.

19. The formulation of claim 13 further comprising a binder.

20. The formulation of claim 13 wherein the preservative is taken from the group consisting of:

Phenoxyethanol,

Methylparaben,

Butylparaben,

Ethylparaben, and

Isobutylparaben.

21. The formulation of claim 13 wherein the emulsifier is taken from the group consisting of:

Cetyl Alcohol,

Cetearyl Alcohol,

Glyceryl Stearate,

Ceteareth-20,

PEG-40 Stearate,

Dicetyl Phosphate,

Ceteth-10 Phosphate.

22. The formulation of claim 16 wherein the thickener is Cetyl Alcohol or Stearyl Alcohol.

23. The formulation of claim 13 wherein:

a) the amount of water ranges from 54% to 90% by weight b) the amount of the quaternary thickener ranges from 0.5% to 5.0% by weight, c) the amount of biocidic agent ranges from 0.25% to 2% by weight, d) the amount of emulsifier ranges from 0.5% to 4% by weight.

* * * * *